United States Patent [19]

Ueda et al.

[11] Patent Number: 5,138,001
[45] Date of Patent: Aug. 11, 1992

[54] VINYLPHENYL COMPOUND, PROCESS FOR THE PRODUCTION THEREOF, POLYMERIZABLE COMPOSITION CONTAINING SAME, AND CROSSLINKED POLYMER FORMED THEREFROM

[75] Inventors: Masahide Ueda; Kanehiro Nakamura; Yoshifumi Matsumoto; Mari Kusaba, all of Tokuyama, Japan

[73] Assignee: Tokuyama Soda Kabushiki Kaisha, Tokuyama, Japan

[21] Appl. No.: 572,454

[22] Filed: Aug. 27, 1990

[30] Foreign Application Priority Data

Aug. 29, 1989 [JP] Japan .................................. 1-220360
Jun. 4, 1990 [JP] Japan .................................. 2-144490

[51] Int. Cl.$^5$ ............................................ C08F 236/20
[52] U.S. Cl. ............................. 526/262; 526/313; 526/328.5; 526/318.2; 526/347
[58] Field of Search ............................... 526/313, 262

[56] References Cited

U.S. PATENT DOCUMENTS 4,785,053 11/1988 Ito ........................................ 525/146
4,961,179 10/1990 Klöcker .............................. 369/288

FOREIGN PATENT DOCUMENTS

63-15811 1/1988 Japan .
64-42447 2/1989 Japan .
2-127408 5/1990 Japan .
1412940 11/1975 United Kingdom .

*Primary Examiner*—Joseph L. Schofer
*Assistant Examiner*—M. Nagumo
*Attorney, Agent, or Firm*—Sherman and Shalloway

[57] ABSTRACT

Novel vinylphenyl compound which gives, as a copolymer with other vinyl compound copolymerizable therewith, a crosslinked polymer excellent in birefringence, transparency, heat resistance and moisture absorption resistance. The crosslinked polymer is advantageously useful as a disk substrate.

5 Claims, 2 Drawing Sheets

VINYLPHENYL COMPOUND, PROCESS FOR THE PRODUCTION THEREOF, POLYMERIZABLE COMPOSITION CONTAINING SAME, AND CROSSLINKED POLYMER FORMED THEREFROM

FIELD OF THE INVENTION

This invention relates to a novel vinylphenyl compound, a process for the production thereof, a polymerizable composition containing same, and a crosslinked polymer formed therefrom.

BACKGROUND OF THE INVENTION

In recent years, optical disks have attracted attention as an information recording medium having a large storage capacity and permitting random access, and have come remarkably into wide use. Such optical disks are grouped into a read only type, a write-once type and a rewritable type. Read only type optical disks are applied, e.g. to video disks, compact disks, etc., and have formed a large-scale market. On the other hand, write-once type and rewritable type disks are applied, e.g. to document, computer and video files. And, development thereof is still under way, although some of them are already on the market. Substrates for such optical disks are required to have excellent properties such as low birefringence, high transparency, high heat resistance and high resistance to moisture absorption. In particular, write-once type and rewritable type optical disks are required to be excellent in the above properties as compared with read only type disks.

PRIOR ART

The present inventors have already proposed a monomer for optical disks by Japanese Laid-Open Patent Publication No. 42447/1989, which discloses a compound of the following formula wherein $R^{11}$, $R^{12}$, $R^{13}$ and $R^{14}$ each independently from each other are a hydrogen atom, a halogen atom or an alkyl group, X' is an oxygen atom, a sulfur atom, a sulfonyl group, an alkylene group, an alkylidene group, or a fluoroalkylidene group, and q and r each are an integer of not less than 1.

The above publication also discloses that polymerization of a mixture of the above compound and a vinyl monomer copolymerizable therewith gives a good optical disk substrate. In order to impart this optical disk substrate with good heat resistance, it is advantageous to increase the content of the above compound in the mixture of the above compound and a copolymerizable vinyl monomer. Since, however, compatibility between the compound of the above formula and a copolymerizable vinyl monomer is, in general, poor at a room temperature, there is a limit of increasing the content of the above compound at a room temperature in order to improve heat resistance. And, even when the compatibility between these two compounds is increased by heating them, e.g. to a temperature of from 100° C. to 120° C., it is necessary to carry out the polymerization while the same temperature is maintained in order to prevent precipitation induced by cooling of the above compound. Therefore, handling of these two compounds is not necessarily easy.

Japanese Laid-Open Patent Publication No. 15811/1988 discloses a polymer of a bisphenol-type vinyl monomer used as a monomer. In this publication, there is disclosed a homopolymer of a monomer of the following formula wherein A represents $R^{21}$ and $R^{22}$ each represent a hydrogen atom or a methyl group, and t and t' each represent zero or an integer of 1 to 10, or a copolymer of at least one of the monomers of the above formula with a monomer copolymerizable therewith as an optical resin having a high refractive index such as a resin for a plastic lens, prism, optical fiber, optical element, and the like.

OBJECT OF THE INVENTION

It is an object of this invention to provide a novel vinylphenyl compound.

It is another object of this invention to provide a novel vinylphenyl compound having excellent compatibility with other vinyl compound copolymerizable therewith and being easy in handling for polymerization.

It is further another object of this invention to provide a novel vinylphenyl compound giving a crosslinked polymer being excellent in birefringence, transparency, heat resistance and resistance to moisture absorption.

It is still another object of this invention to provide a polymerizable composition of a vinylphenyl compound of this invention and other vinyl compound copolymerizable therewith, which is easy in handling and gives a crosslinked polymer having excellent properties described above.

It is yet another object of this invention to provide a crosslinked polymer containing polymerized units of a vinylphenyl compound of this invention and having excellent properties described above.

Further, it is another object of this invention to provide a thin plate, e.g. an optical disk substrate, which is formed of the above crosslinked polymer of this invention.

It is further another object of this invention to provide an industrially advantageous process for the production of the vinylphenyl compound of this invention.

Other objects and advantages of this invention will be apparent from the following description.

The above objects and advantages of this invention are firstly achieved by a vinylphenyl compound of the following formula (I).

12 carbon atoms or an aralkyl group having 7 to 10 carbon atoms.

Preferred examples of the aryl group are nonsubstituted aryl groups such as phenyl, naphthyl and biphenyl groups, a phenyl group substituted with an alkyl group having 1 to 6 carbon atoms, a naphthyl group substituted with a methyl or ethyl group. The alkyl group having 1 to 6 carbon atoms may be linear or branched. Examples of such an alkyl group are methyl, ethyl, n-propyl, iso-propyl, n-butyl, n-pentyl and n-hexyl groups. The phenyl group may be substituted with 1 to 5 alkyl groups provided that the total number of the carbon atoms of the substituent alkyl group is up to six. As a phenyl group substituted with an alkyl having 1 to 6 carbon atoms, for example, tolyl and xylyl groups are preferred.

As the aralkyl group having 7 to 10 carbon atoms, preferred is, e.g. an alkyl group having 1 to 4 carbon atoms which is substituted with a phenyl group. Specific examples of such an aralkyl group are benzyl, phenylethyl, phenylpropyl and phenylbutyl groups.

In the formula (I), $R^2$, $R^3$, $R^4$, $R^5$ and $R^6$ each may be identical to or different from each other and each is a hydrogen atom or an alkyl group having 1 to 4 carbon (I)

wherein $R^1$ is an aryl group having 6 to 12 carbon atoms or an aralkyl group having 7 to 10 carbon atoms, $R^2$, $R^3$, $R^4$, $R^5$ and $R^6$ may be identical to or different from each other and each is a hydrogen atom or an alkyl group having 1 to 4 carbon atoms, and m and n each are independently an integer of not less than 1.

DETAILED DESCRIPTION OF THE INVENTION

In the above formula (I) for the vinylphenyl compound of this invention, $R^1$ is an aryl group having 6 to atoms. The alkyl group having 1 to 4 carbon atoms may be linear or branched. Examples of such an alkyl group are methyl, ethyl, n-propyl, isopropyl, n-butyl, sec-butyl, iso-butyl and tert-butyl groups.

Further, in the formula (I), each of m and n is independently an integer of not less than 1. Each of m and n is preferably, independently of the other, an integer of 1 to 4, particularly preferably 1. Vinylphenyl compounds of the formula (I) in which m and n are 1 to 4, particularly 1, are easily available.

The vinylphenyl compounds of the invention have properties different to some extent depending upon $R^1$ to $R^6$, m and n of formula (I). In general, however, these compounds are light yellow or white solids at a room temperature under an atmospheric pressure.

The vinylphenyl compounds of the invention are, in general, soluble in an organic solvent such as benzene, chloroform, toluene, tetrahydrofuran, or the like, but sparingly soluble in an alcohol such as methanol, ethanol, or the like and water.

Preferred examples of the vinylphenyl compound of this invention are as follows.

-continued

-continued

According to this invention, the compound of the above formula (I) can be produced by a reaction between a bisphenol compound of the following formula (II)

wherein $R^1$ is an aryl group having 6 to 12 carbon atoms or aralkyl group having 7 to 10 carbon atoms, and $R^2$, $R^4$ and $R^5$ may be identical to or different from each other and each is a hydrogen atom or an alkyl group having 1 to 4 carbon atoms, and a vinyl compound of the following formula (III)

wherein $R^7$ is a hydrogen atom or an alkyl group having 1 to 4 carbon atoms, X is a halogen atom, and k is an integer of not less than 1.

In the above formula (II), $R^1$, $R^2$, $R^4$ and $R^5$ are as defined in the above formula (I).

Preferred examples of the compound of the formula (II) are bis(4-hydroxyphenyl)phenylmethane, 1,1-bis(4-hydroxyphenyl)-1-phenylethane, 1,1-bis(4-hydroxyphenyl)-1-(4-methylphenyl)ethane, 1-biphenyl-1,1-bis(4-hydroxyphenyl)ethane, 1,1-bis(3-methyl-4-hydroxyphenyl)-1-phenylethane, 1-phenyl-2,2bis(4-hydroxyphenyl)propane, 1,1-bis(4-hydroxyphenyl)-2-phenylethane, 1,1-bis(4-hydroxyphenyl)-1-(4-ethylphenyl)ethane, 1,1-bis(4-hydroxyphenyl)-1-(4-n-propylphenyl)ethane, 1,1-bis(4-hydroxyphenyl)-1-(4-isopropylpheny)ethane, 1,1-bis(4-hydroxyphenyl)-1-(4-t-butylphenyl)ethane, 1,1-bis(4-hydroxyphenyl)-1-(4-n-pentylphenyl)ethane, 1,1-bis(4-hydroxyphenyl)-1-(4-n-hexylphenyl)ethane, 1,1-bis(4-hydroxyphenyl)-1-(2,4-dimethylphenyl)ethane, 1,1-bis(4-hydroxyphenyl)-1-(2,4,6-trimethylphenyl)ethane, 1,1-bis(4-hydroxyphenyl)-1-(2,4-diethylphenyl)ethane, 1-[1,1-bis(4-hydroxyphenyl)ethyl]naphthalene, 2-[1,1-bis(4-hydroxyphenyl)ethyl]naphthalene, 2-[1,1-bis(4-hydroxyphenyl)ethyl]-8-methylnaphthalene, 1,1-bis-(4-hydroxyphenyl)-1-phenylpropane, 1,1-bis(4-hydroxyphenyl)-1-phenylbutane, 1,1-bis(4-hydroxyphenyl)-1-phenylpentane, 1,1-bis(4-hydroxyphenyl)-1-phenyl-2-methylpropane, 1,1-bis(4-hydroxyphenyl)-1-phenyl-2,2-dimethylpropane, 1,1-bis(4-hydroxyphenyl)-3-phenylpropane, 1,1-bis(4-hydroxyphenyl)-4-phenylbutane, 1,1-bis(4-hydroxyphenyl)-3-methyl-3-phenylpropane, 1,1-bis(3-ethyl-4-hydroxyphenyl)-1-phenylethane, 1,1-bis(3-n-propyl-4-hydroxyphenyl)-1-phenylethane, 1,1-bis(3-isopropyl-4-hydroxyphenyl)-1-phenylethane, 1,1-bis(3-n-butyl-4-hydroxyphenyl)-1-phenylethane, 1,1-bis(3-sec-butyl-4-hydroxyphenyl)-1-phenylethane, 1,1-bis(3-tert-butyl-4-hydroxyphenyl)-1-phenylethane, and 1,1-bis(2-methyl-4-hydroxyphenyl)-1-phenylethane.

In the above formula (III), $R^7$ is a hydrogen atom or an alkyl group having 1 to 4 carbon atoms, X is a halogen atom, and k is an integer of not less than 1.

Examples of the alkyl having 1 to 4 carbon atoms are as exemplified previously.

As the halogen atom, for example, chlorine and bromine atoms are preferred.

The suffix "k" is an integer of not less than 1, preferably 1 to 4, particularly preferably 1.

Examples of the compound of the formula (III) are p-chloromethylstyrene, m-chloromethylstyrene, p-bromomethylstyrene, m-bromomethylstyrene and a mixture of these; p-iodomethylstyrene, m-iodomethylstyrene and a mixture of these; p-chloroethylstyrene, m-chloroethylstyrene and a mixture of these, p-bromoethylstyrene, m-bromoethylstyrene and a mixture of these; p-iodoethylstyrene, m-iodoethylstyrene and a mixture of these; 2-methyl-4-chloromethylstyrene, 3-chloromethyl-5-methylstyrene, 3-methyl-4-chloromethylstyrene, 3-chloromethyl-4-methylstyrene, 2-ethyl-4-chloromethylstyrene, 3-chloromethyl-5-ethylstyrene, 3-ethyl-4-chloromethylstyrene, 3-chloromethyl-4-ethylstyrene and a mixture of these; and the like.

The compounds of the above formulae (II) and (III) are either known or can be easily produced according to processes known per se.

The reaction beween the bisphenol compound of the formula (II) and the vinyl compound of the formula (III) is performed stoichiometrically in a bisphenol compound/vinyl compound molar ratio of 1:2. In general, however, the vinyl compound of the formula (III) is used in an amount equimolar to 10 times by mole, preferably 2 times by mole or in a little excess of 2 times by mole, based on the bisphenol compound of the formula (II).

In this invention, the solvent used for the above reaction is not particularly limited. Preferred examples of the solvent are aromatic or aliphatic hydrocarbons such as benzene, toluene, xylene, hexane, heptane and petroleum ether; ethers such as diethyl ether, dioxane and tetrahydrofuran; ketones such as acetone and methyl ethyl ketone; alcohols such as methanol, ethanol and n-butanol; nitriles such as acetonitrile; N,N-dialkylamides such as N,N-dimethylformamide and N,N-diethylformaide; dimethyl sulfoxide; and water.

The above reaction is carried out preferably in the presence of a base. Particularly preferred is a process which comprises reacting a bisphenol compound of the formula (II) with a base to form a bisphenoxide and then, reacting it with a vinyl compound of the formula (III). Preferred examples of the base are alkali metals such as sodium and potassium; metal salts such as sodium hydroxide, potassium hydroxide, sodium carbonate, potassium carbonate, barium carbonate and silver oxide; amines such as trimethylamine and triethylamine; sodium amide; sodium hydride; and the like. The amount of the base used is, in general, equimolar to 10 times by mole, preferably 2 times by mole or a little excess of 2 times by mole, based on the bisphenol compound of the formula (II).

The above reaction is carried out preferably in the presence of a catalyst. Usable as the catalyst are those which are known for the ether bond formation reaction by dehydrohalogenation. Sodium iodide and potassium iodide are preferred. The amount of the catalyst used is, in general, 1 mol % to equimolar, preferably 5 mol % or a little larger than 5 mol %, based on the vinyl compound of the formula (III).

The temperature for the above reaction is such an temperature that the vinyl compound of the formula (III) does not undergo polymerization during the reaction, and it is preferably between $-20°$ C. and $80°$ C., more preferably $0°$ C. and $40°$ C. The reaction time is preferably 5 minutes to 10 days, more preferably 1 to 40 hours although it differs depending upon materials. Further, it is preferable to stir a reaction mixture during the reaction.

The intended product, i.e. the compound of the formula (I) can be isolated from a reaction system and purified according to known methods. For example, the reaction liquid is cooled or left to stand at room temperature or a temperature in the vicinity thereof, a reaction solvent is distilled off, and the resultant residue is subjected to extraction with methylene chloride. This procedure removes an unreacted bisphenol compound and by-products such as salts and high-molecular weight compounds. The methylene chloride phase is dried over a desiccant such as Glauber's salt or calcium chloride, the methylene chloride is then distilled off, and the resultant residue is recrystallized, whereby the intended product can be obtained.

The structure of the compound of the formula (I) can be determined by the following means.

(a) A sample compound is measured for an infrared absorption spectrum (ir), whereby absorption of an aryl alkyl ether due to reversely symmetrical elongation and shrinkage of C—O—C bonds is observed at 1,200 cm$^{-1}$ to 1,275 cm$^{-1}$.

(b) A sample compound is measured for a mass spectrum (ms), and composition of fragment ions is determined from the observed peaks (value of m/e: m=mass of ions, e=valence of ions), whereby it is possible to assume a molecular weight of the sample compound and a bonding form of atomic groups of the molecule thereof. That is, when the sample compound has a molecular weight of M, an ion peak is observed at and M$^{\oplus}$ position or a pseudo ion peak at an $(M \pm 1)^{\oplus}$ position.

Further, a characteristic intense peak corresponding to is observed. Thus, the bonding form of the molecule can be determined.

(c) $^1$H-nuclear magnetic resonance spectrum ($^1$H—NMR) is measured, whereby bonding forms of hydrogen atoms present in the compounds of the formula (I) can be determined. The following is the result of $^1$H—NMR analysis (δ, ppm: tetramethylsilane as standard, deutero chloroform as a solvent) of 1,1-bis(4-vinylbenzyloxyphenyl)-1-phenylethane as a typical example of compounds of the formula (I).

That is, a singlet for three protons is observed at 2.1 ppm, and assigned to a methyl group (g). A singlet for four protons is observed at 5.0 ppm, and assigned to a methylene group (e) of a benzyl group. A quadruplet for two protons is observed in the vicinity of 5.1 ppm to 5.4 ppm, and assigned to a proton (b) of which the signal is split by a proton (a) (J-11 Hz) and a proton (c) (J-2 Hz). A quadruplet for two protons is observed in the vicinity of 5.5 ppm to 5.9 ppm, and assigned to a proton (c) of which the signal is splitted by a proton (a) (J-18 Hz) and a proton (b) (J-2 Hz). A multiplet for 15 protons is observed at 6.5 to 7.3 ppm and assigned to a proton (a) intensely unshielded with a benzene ring and protons (f) substituted in benzene rings. A singlet for 8 protons is observed at 7.4 ppm, and assigned to protons (d) substituted in a benzene ring.

(d) A weight percent of carbons and a weight percent of hydrogen atoms are determined by elemental analysis, and the total sum of the resultant weight percents is deducted from 100 to give a weight percent of oxygen atoms.

The vinylphenyl compound of the formula (I), provided by this invention, can give a homopolymer when polymerized alone, and it can also give a copolymer when polymerized with other vinyl compound copolymerizable therewith.

The vinylphenyl compound of the formula (I) can give a homopolymer by undergoing heat polymerization alone, radical polymerization in the presence of an initiator such as peroxide, an azo compound or the like, or photopolymerization in the presence of a photopolmerization initiator. The initiators which will be discussed later can be used without any limitation to the kind and the amount. There is no particular limitation on the method for the above polymerizations. In general, melt-polymerization and cast-polymerization can be preferably used.

Examples of the other vinyl compound copolymerizable with the vinylphenyl compound of the formula (I)

include various monomers, and in particular, any conventionally known monomers for use in cast-polymerization for disk substrates, etc., can be used without any limitation.

Examples of such a polymerizable vinyl compound are styrene and derivatives thereof such as vinyl toluene, α-methylstyrene, chlorostyrene, fluorostyrene, bromostyrene, butylstyrene, trans-stilbene and divinylbenzene; acrylates, methacrylates and derivatives thereof such as methyl methacrylate, ethyl methcrylate, butyl methacrylate, phenyl methacrylate, benzyl methacrylate, cyclohexyl methacrylate, bornyl methacrylate, isobornyl methacrylate, methyl acrylate, ethyl acrylate, butyl acrylate, phenyl acrylate, benzyl acrylate, cyclohexyl acrylate, bornyl acrylate, isobornyl acrylate, a compound of the following formula (a)

(a)

wherein B is an acryloyl or methacryloyl group, and u is an integer of not less than 0,
a compound of the following formula (b)

(b)

wherein B and u are as defined in the above formula (a), and v is an integer of not less than 0,
and a compound of the following formula (c)

(c)

wherein $R^{31}$ and $R^{32}$ each are independently a hydrogen atom or a methyl group, and u and v each are an integer of not less than 0;
(meth)allyl ethers such as a compound of the following formula (d)

(d)

wherein B' is an allyl or methallyl group, and u is an integer of not less than 0;
and a compound of the following formula (e)

(e)

wherein B' and u are as defined in the above formula (d), and v is an integer of not less than 0;
maleic acid and derivatives thereof such as maleic anhydride and phenylmaleic anhydride; and maleimide derivatives such as N-methylmaleimide and N-phenylmaleimide.

Of these compounds, styrene and its derivatives are preferred in view of production of desired copolymers with the compound of the formula (I) and production of disk substrates whose hygroscopicity is low. In addition, in order to improve other properties of an intended disk substrate, it is possible to jointly use other monomer copolymerizable with the above vinyl monomer.

The compound of the formula (I) is easily soluble in other vinyl monomers copolymerizable therewith at a room temperature. The mixing ratio of these two compounds ranges widely. In order to obtain full effects of this invention, the mixing ratio of the compound of the formula (I) to the other vinyl monomer copolymerizable therewith is 5 to 75% by weight to 95 to 25% by weight.

According to this invention, therefore, there is provided a polymerizable composition which comprises a vinylphenyl compound (A) of formula (I) and other vinyl compound (B) copolymerizable with the vinylphenyl compound (A), the composition containing, based on the total weight of the vinylphenyl compound (A) and the other vinyl compound (B), 5 to 75% by weight, preferably 20 to 70% by weight of the vinylphenyl compound (A) and 95 to 25% by weight, preferably 80 to 30% by weight of the other vinyl compound (B).

In order to decrease birefringence, especially the birefringence measured at 30° incident angle of light ray while maintaining heat resistance and low hygroscopicity, it is preferable to use 30 to 65% by weight of the compound of the formula (I), 10 to 50% by weight of styrenes as the other vinyl compound and 5 to 50% by weight of a compound selected from (iso)bornyl methacrylate, (iso)bornyl acrylate, polycyclic hydrocarbon-containing compounds of the formulae (a) and (b).

The above copolymerizable compound of this invention gives a crosslinked polymer of this invention by heating it in the presence of an initiator such as an organic peroxide or an azo compound.

The crosslinked polymer of this invention comprises polymerized units (A') derived from the vinylphenyl compound of the formula (I) and polymerized units (B') of the above copolymerizable, other vinyl compound.

Examples of the initiator include organic peroxides and azo compounds. Examples of the organic peroxides are dialkyl peroxides such as di-t-butyl peroxide, t- butylcumyl peroxide, dicumyl peroxide, 2,5-dimethyl-2,5-di-(t-butylperoxy)-hexane, 1,3-bis(t-butylperoxy-isopropyl)benzene, 2,2-di-t-butylperoxybutane; alkyl peresters such as t-butyl peracetate, t-butyl perisobutylate, t-butyl peroctoate, t-butyl perbenzoate, and t-butylperoxy-3,5,5-trimethylhexate; and percarbonates such as diisopropylperoxydicarbonate, bis(4-t-butylcyclohexyl)peroxydicarbonate, and di-3-methoxybutyl-peroxydicarbonate. And, examples of the azo compounds are 2,2'-azobis(2-amidinopropane)diacetate, 2,2'-azobis(2-amidinopropane)dihydrochloirde, 2,2'-azobisisobutyronitrile, 1,1'-azobis(cyclohexane-1-carbonitrile), 2,2'-azobis(2,4-dimethylvaleronitrile), 2,2'-azobis(4-methoxy-2,4-dimethylvaleronitrile) and 2,2'-azobis(methylisobutyrate).

These initiators can be used in an amount of 0.01 to 5% by weight based on the total amount of the monomers.

The above crosslinked polymer of this invention can be advantageously produced, e.g. by cast-polymerization. That is, an intimate mixture of a polymerizable composition with an initiator is prepared, and the mixture is charged into a polymerization mold. After degassing, the polymerization is carried out at a predetermined temperature for a predetermined period of time. In this case, a metal base plate having guide grooves or pits engraved may be used as a polymerization mold, whereby the grooves or pits are replicated directly on a substrate. Otherwise, a thin plate having a predetermined thickness, which is prepared by cast-polymerization, may be formed, and then disks having a predetermined size may be cut out from the plate. Further, a crosslinked polymer of this invention may be formed as follows. A photosensitizer is incorporated into a co-polymerizable composition of this invention, and the mixture is charged into a glass mold having a predetermined space. Then, the mixture is polymerized by irradiating it with UV light, radiation, or the like.

The copolymerizable composition of this invention may contain an antioxidant, a photostabilizer, a mold releaser, an antistatic agent, etc., as far as these components do not impair the objects of this invention.

The vinylphenyl compound of the formula (I), provided by this invention, can not only give the crosslinked polymer of this invention having excellent properties when polymerized with other vinyl compound copolymerizable with the vinylphenyl compound, but also can give a homopolymer having excellent properties. The homopolymer structurally contains a number of aromatic rings in the molecule and has a small oxygen content. Therefore, it gives a crosslinked polymer having a high refractive index and having little water absorption property and excellent dimensional stability. Namely, when the vinylphenyl compound of the formula (I) is homopolymerized, it is possible to produce a crosslinkable resin for optical use which has properties of transparency, high refractive index and low water absorption, and the resin can be applied to plastic lenses, prism, optical fibers, optical disk substrates, optical elements, and the like.

The vinylphenyl compound of the formula (I), provided by this invention, is easily soluble in other vinyl copolymerizable monomer at a room temperature. It is therefore possible to obtain a mixture containing the vinylphenyl compound of the formula (I) in a larger amount than the other copolymerizable vinyl monomer. Consequently, it is possible to obtain a polymer containing polymerized units derived from the vinylphenyl compound, which has more excellent heat resistance and moisture absorption resistance. Furthermore, the vinylphenyl compound of the formula (I) has high solubility at a room temperature, and it is therefore free from precipitation when cooled during a polymerization procedure.

A preferred copolymer produced from the vinylphenyl compound of the formula (I) as a crosslinking agent and other copolymerizable vinyl monomer has the following excellent properties as an optical organic glass. That is, it has a birefringence, measured at perpendicular incident light ray, of not more than 15 nm, not more than 10 nm in particular, a birefringence, measured at 30° incident angle of light ray, of not more than 100 nm, not more than 50 nm in particular, a total light transmissivity of not less than 85%, not less than 90% in particular, a glass transition temperature of not less than 100° C., not less than 130° C. in particular, and a water absorptivity of not more than 0.2%, not more than 0.1% in particular.

Therefore, the vinylphenyl compound of the formula (I), provided by this invention, is suitable for use in the production of not only an optical disk for use in the production of not only an optical disk substrate but also optical lenses such as lenses for glasses, lenses for optical apparatus, etc., and optical organic glass products such as prism, optical fibers, etc. The thin plate formed of the crosslinked polymer of this invention can be advantageously used as an optical disk substrate.

EXAMPLES

This invention will be explained further specifically by reference to Examples and Comparative Examples. However, this invention shall not be limited thereto.

EXAMPLE 1

A 3-liter flask was charged with 0.5 mol of p-chloromethylstyrene, 1 mol of 1-phenyl-1,1-bis(4-hydroxyphenyl)ethane as bisphenol, 1 mol of sodium hydroxide, 0.05 mol of potassium iodide and 1,000 ml of methanol, and the mixture was allowed to react at room temperature for 15 hours. After the reaction, the reaction mixture was cooled, and the resultant precipitate was filtered. An intended product in the filtrate was extracted with methylene chloride, and the extraction solution was washed with diluted aqueous sodium hydroxide and then with water, and dried over anhydrous sodium sulfate. Then, the methylene chloride was distilled off under reduced pressure, and the intended product was recrystallized from acetonemethanol to give white crystals.

Figure 1:
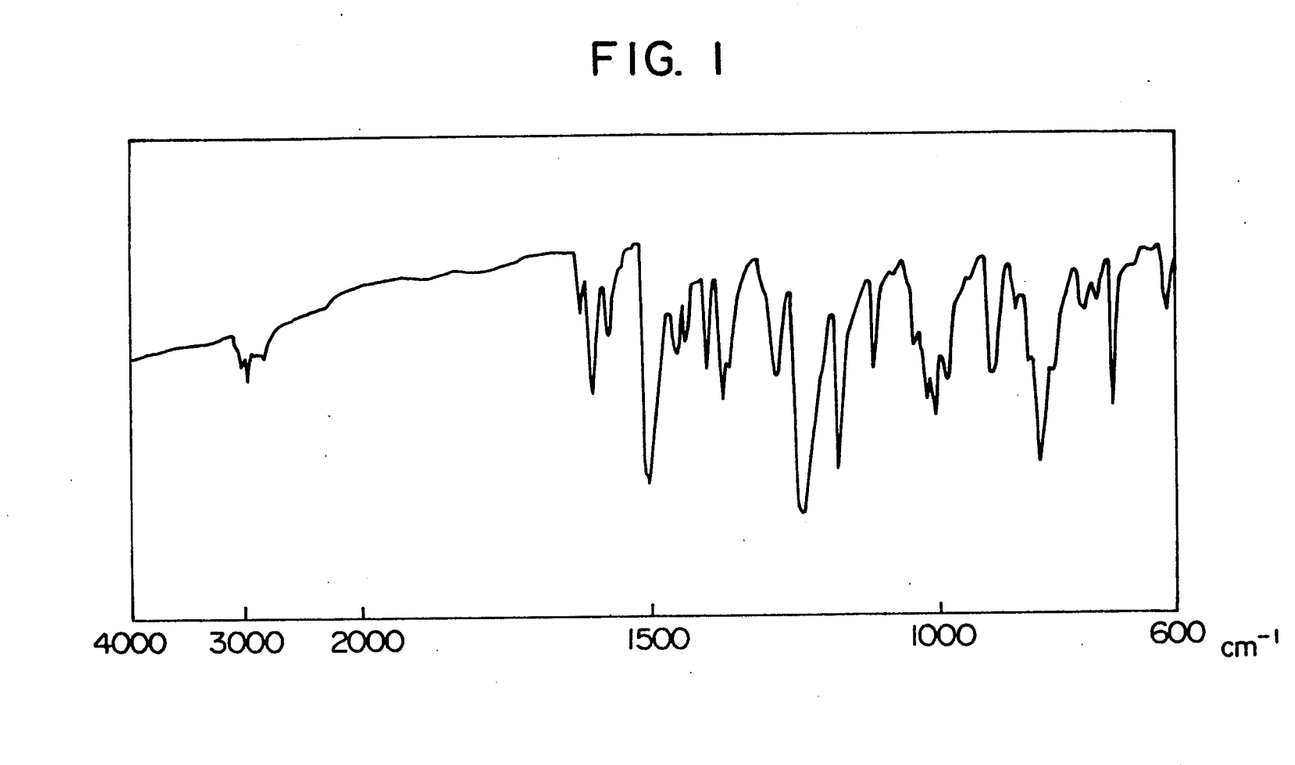
FIG. 1 shows an infrared absorption spectrum of one example of the vinylphenyl compound of this invention (Example 1).

FIG. 1 shows an infrared absorption spectrum of the crystal compound, which showed intense absorption caused by a C—O—C bond in the vicinity of 1,240 cm$^{-1}$. No absorption based on —OH was shown.

Elemental analysis of the compound showed C=87.26% and H=6.65%, which was well in agreement with calculated values C=87.32% and H=6.56% based on the composition formula $C_{38}H_{34}O_2$ (522.69).

And, the compound was measured for a mass an intense peak corresponding to at m/e 117.

Figure 2:
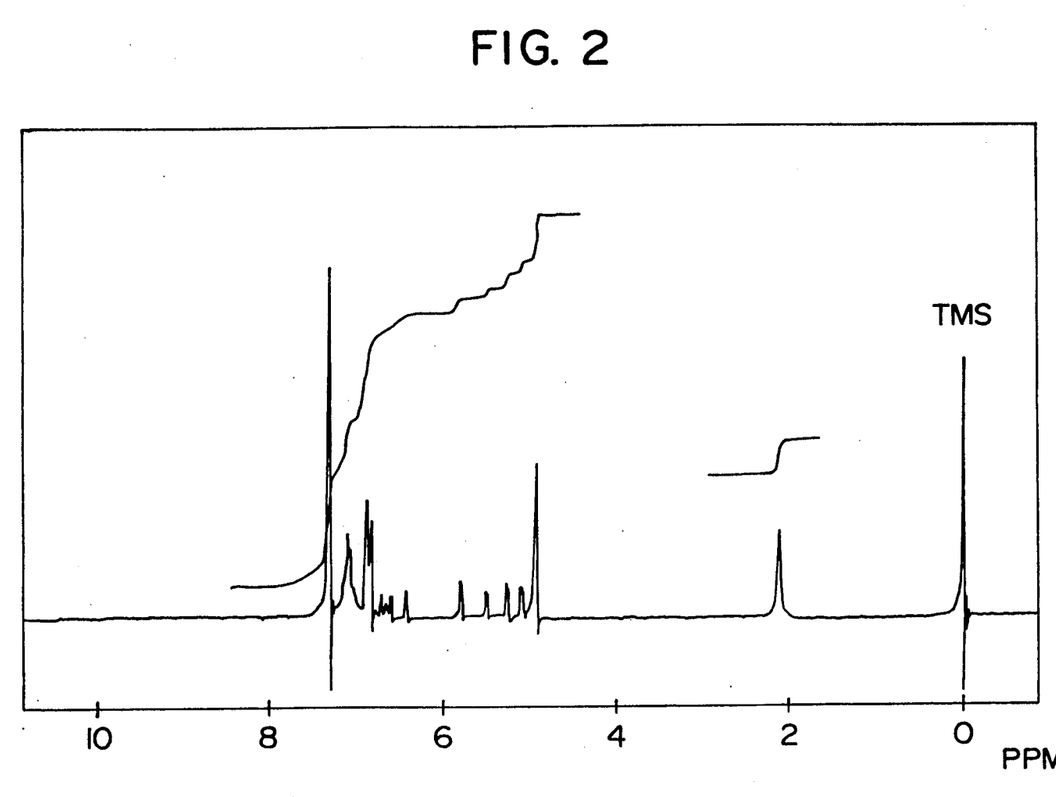
FIG. 2 is a chart showing $^1$H—NMR spectrum of one example of the vinylphenyl compound of this invention (Example 1).

Further, FIG. 2 shows a ¹H-nuclear magnetic resonance spectrum (δ; ppm: tetramethylsilane as standard, deutero chloroform solvent) of the compound. The analysis shows the following.

That is, a singlet for three protons was observed at 2.1 ppm, and assigned to a methyl group (g). A singlet for four protons was observed at 5.0 ppm, and assigned to a methylene group (e) of a benzyl group. A quadruplet for two protons was observed in the vicinity of 5.1 ppm to 5.4 ppm, and assigned to a proton (b) of which the signal was splitted by a proton (a) (J-11 Hz) and a proton (c) (J-2 Hz). A quadruplet for two protons was observed in the vicinity of 5.5 ppm to 5.9 ppm, and assigned to a proton (c) of which the signal was splitted by a proton (a) (J-18 Hz) and a proton (b) (J-2 Hz). A multiplet for 15 protons was observed at 6.5 to 7.3 ppm and assigned to a proton (a) intensely unshielded with a benzene ring and protons (f) substituted in benzene rings. A singlet for 8 protons was observed at 7.4 ppm, and assigned to protons (d) substituted in a benzene ring.

The above results shows that the isolated product was 1,1-bis(4-vinylbenzyloxyphenyl)-1-phenylethane (to be referred to as CS-A hereinafter).

EXAMPLES 2-7

Example 1 was repeated except for use, as bisphenol, of one of bis(4-hydroxyphenyl)phenylmethane, bisphenol, of one of bis(4-hydroxyphenyl)phenylmethane, 1,1-bis(4-hydroxyphenyl)-1-(4-methylphenyl)ethane, 1-biphenyl-1,1-bis(4-hydroxyphenyl)ethane, 1,1-bis(3-methyl-4-hydroxyphenyl)-1-phenylethane, 1-phenyl-2,2-bis(4-hydroxyphenyl)propane, and 1,1-bis(4-hydroxyphenyl)-2-phenylethane, whereby various vinylphenyl compounds were produced. Table 1 shows the structural formulae of the vinylphenyl compounds and the results of ¹H—NMR analysis and elemental analysis thereof.

TABLE 1

| Ex. | Biphenyl compound (structural formula) | ¹H-NMR | Elemental analysis (%) Found C | Found H | Calculated C | Calculated H |
|---|---|---|---|---|---|---|
| 2 | (CS-B) | δ = 5.0PPM(4H (e))<br>= 5.1-5.4PPM(2H (b))<br>= 5.5PPM(1H (g))<br>= 5.5-5.9PPM(2H (c))<br>= 6.5-7.3PPM(15H (a) and (f))<br>= 7.4PPM(8H (d)) | 87.43 | 6.19 | 87.37 | 6.34 |
| 3 | (CS-C) | δ = 2.1PPM(3H (f))<br>= 2.3PPM(3H (g))<br>= 5.0PPM(4H (e))<br>= 5.1-5.4PPM(2H (b))<br>= 5.5-5.9PPM(2H (c))<br>= 6.5-7.3PPM(14H (a) and (f))<br>= 7.4PPM(8H (d)) | 87.43 | 6.59 | 87.28 | 6.76 |
| 4 | (CS-D) | δ = 2.1PPM(3H (g))<br>= 5.0PPM(4H (e))<br>= 5.1-5.4PPM(2H (b))<br>= 5.5-5.9PPM(2H (c))<br>= 6.5-7.6PPM(27H (a) and (d)) | 88.09 | 6.51 | 88.26 | 6.40 |

TABLE 1-continued

| Ex. | Biphenyl compound (structural formula) | $^1$H-NMR | Elemental analysis (%) Found C | Found H | Calculated C | Calculated H |
|---|---|---|---|---|---|---|
| 5 | (CS-E) | δ = 2.1PPM(2H (g))<br>= 2.2PPM(6H (f))<br>= 5.0PPM(4H (e))<br>= 5.1–5.4PPM(2H (b))<br>= 5.5–5.9PPM(2H (c))<br>= 6.5–7.3PPM(13H (a) and (h))<br>= 7.4PPM(8H (d)) | 87.23 | 6.90 | 87.24 | 6.95 |
| 6 | (CS-F) | δ = 2.1PPM(3H (f))<br>= 4.0PPM(2H (g))<br>= 5.0PPM(4H (e))<br>= 5.1–5.4PPM(2H (b))<br>= 5.5–5.9PPM(2H (c))<br>= 6.5–7.3PPM(15H (a) and (h))<br>= 7.4PPM(8H (d)) | 87.09 | 6.53 | 87.28 | 6.76 |
| 7 | (CS-G) | δ = 4.0PPM(2H (g))<br>= 5.0PPM(4H (e))<br>= 5.1–5.4PPM(2H (b))<br>= 5.5PPM(1H (f))<br>= 5.5–5.9PPM(2H (c))<br>= 6.5–7.3PPM(15H (a) and (h))<br>= 7.4PPM(8H (d)) | 87.38 | 6.42 | 87.32 | 6.56 |

EXAMPLE 8

Example 1 was repeated except for use, as a vinyl compound, of a chloromethylstyrene mixture having a m-form/p-form molar ratio of 6/4, whereby a vinyl compound was obtained. The following are the structural formula of the resultant vinylphenyl compound and the results of $^1$H—NMR analysis and elemental analysis thereof.

$$\frac{\text{m-form}}{\text{p-form}} \text{ (molar ratio)} \approx \frac{6}{4}$$

$^1$H-NMR
δ = 2.1PPM(3H (g))
= 5.0PPM(4H (e))
= 5.1–5.4PPM(2H (b))
= 5.5–5.9PPM(2H (c))
= 6.5–7.3PPM(15H (a) and (f))
= 7.4PPM(8H (d))

TABLE 2

| Elemental analysis (%) | C | H |
|---|---|---|
| Found | 87.45 | 6.41 |
| Calculated | 87.32 | 6.56 |

EXAMPLES 9–19 and COMPARATIVE EXAMPLES 1–7

The vinylphenyl compounds of this invention produced in Examples 1 to 8 were used to produce polymers.

In each case, the vinylphenyl compound and a vinyl monomer copolymerizable therewith were mixed in a mixing ratio shown in Table 3 at 20° C. Then, 0.3 part of 1-hydroxycyclohexyl phenyl ketone as a polymerization initiator was added, and the mixture was degassed. Thereafter, the mixture was charged into a mold composed of two glass sheets and a Teflon tube, and polymerized by UV irradiation. After the polymerization, a polymer was released from the mold to give a colorless transparent disk substrate having a thickness of 1.2 mm and a diameter of 130 mm.

Table 3 shows physical properties of the resultant disk substrates.

Table 3 also shows physical properties of disk substrates produced by using a conventional cross-linking agent.

The disk substrate materials were measured for physical properties according to the following test methods.

(i) Birefringence: A plate having a thickness of 1.2 mm was prepared, and measured for birefringences of perpendicular incident of light ray and at 30° incident angle of right ray by using a high-accuracy automatic birefringence measuring apparatus.

(ii) Total light transmissivity: A plate having a thickness of 1.2 mm was prepared, and measured according to JIS-K-7105.

(iii) Glass transition temperature: Measurement was made by using a differential scanning calorimeter.

(iv) Water absorptivity: Measurement was made according to JIS-K-6911.

alcohol with a methacrylic or acrylic acid were mixed in a mixing ratio shown in Table 4 at a suitable temperature. And, the procedure of Example 9 was repeated to give a disk substrate. Table 4 shows physical properties of the disk substrate obtained in each of Examples 20 to 28. The physical properties were measured in the same way as in Example 9.

TABLE 4

| | Vinylphenyl compound (parts by weight) | | Styrene monomer (parts by weight) | | (meth)Acrylate (parts by weight) | | Birefringence (nm) | | Total light transmissivity (%) | Glass transition temperature (°C.) | Water absorptivity (%) |
|---|---|---|---|---|---|---|---|---|---|---|---|
| | | | | | | | Perdendicular incident light ray | 30° angle incident light ray | | | |
| 20 | CS-A | (40) | styrene | (40) | IBMA | (20) | <5 | 20–30 | 90 | 138 | 0.08 |
| 21 | CS-A | (50) | styrene | (30) | IBMA | (20) | <5 | 20–30 | 90 | 140 | 0.07 |
| 22 | CS-A | (60) | styrene | (30) | IBA | (10) | <5 | 15–25 | 90 | >150 | 0.06 |
| 23 | CS-A | (50) | styrene | (20) | IBMA | (30) | <5 | 10–20 | 90 | 142 | 0.10 |
| 24 | CS-A | (50) | methyl-styrene | (30) | IBMA | (20) | <5 | 20–30 | 90 | 135 | 0.08 |
| 25 | CS-H | (50) | styrene | (30) | IBMA | (20) | <5 | 20–30 | 90 | 139 | 0.08 |
| 26 | CS-A | (40) | styrene | (40) | TCDDA | (20) | <5 | 20–30 | 90 | >150 | 0.10 |
| 27 | CS-A | (50) | styrene | (20) | TCDDA | (30) | <5 | <10 | 90 | >150 | 0.12 |
| 28 | CS-A | (50) | styrene | (30) | DCPMA | (20) | <5 | 20–30 | 90 | 143 | 0.08 |

The abbreviations in Table 4 stand for the following.
IBMA: Isoborynyl methacrylate
IBA: Isobornyl acrylate
TCDDA: Bis(oxymethyl)tricyclo[5,2,1,0$^{2,6}$]decane diacrylate
DEPMD: Dicyclopentanyl methacrylate

EXAMPLES 29–36 and COMPARATIVE EXAMPLES 8–10

CS-A or a mixture of CS-A with a vinyl monomer copolymerizable therewith was mixed with 0 to 4 parts by weight of p-methoxyphenol as a polymerization

TABLE 3

| | | Vinylphenyl compound (parts by weight) | | Vinyl monomer (parts by weight) | | Birefringence (nm) | | Total light transmissivity (%) | Glass transition temperature (°C.) | Water absorptivity (%) |
|---|---|---|---|---|---|---|---|---|---|---|
| | | | | | | Perdendicular incident light ray | 30° angle incident light ray | | | |
| Example | 9 | CS-A | (30) | styrene | (70) | <10 | 50–60 | 90 | 125 | 0.05 |
| | 10 | CS-A | (35) | styrene | (65) | <10 | 40–50 | 90 | 134 | 0.05 |
| | 11 | CS-A | (40) | styrene | (60) | <5 | 30–40 | 90 | 142 | 0.05 |
| | 12 | CS-H | (60) | styrene | (40) | <5 | 20–30 | 90 | >150 | 0.08 |
| | 13 | CS-H | (70) | styrene | (30) | <5 | <20 | 90 | >150 | 0.09 |
| | 14 | CS-C | (35) | styrene | (65) | <10 | 40–50 | 90 | 132 | 0.05 |
| | 15 | CS-D | (35) | styrene | (65) | <10 | 40–50 | 90 | 130 | 0.05 |
| | 16 | CS-E | (35) | styrene | (65) | <10 | 40–50 | 90 | 132 | 0.05 |
| | 17 | CS-F | (35) | styrene | (65) | <10 | 40–50 | 90 | 132 | 0.05 |
| | 18 | CS-G | (35) | styrene | (65) | <10 | 40–50 | 90 | 134 | 0.05 |
| | 19 | CS-H | (35) | styrene | (65) | <10 | 40–50 | 90 | 134 | 0.05 |
| Comparative Example | 1 | DVB | (30) | styrene | (70) | 15–30 | 150–200 | 90 | 125 | 0.05 |
| | 2 | EGDMA | (30) | styrene | (70) | 15–30 | 120–150 | 90 | 140 | 0.21 |
| | 3 | BPADMA | (30) | methyl-styrene | (70) | 15–30 | 100–120 | 90 | 132 | 0.20 |
| | 4 | HDDSME | (30) | styrene | (70) | 15–30 | 100–120 | 90 | 110 | 0.07 |
| | 5 | BPADSME | (10) | styrene | (90) | 15–30 | 80–100 | 90 | 101 | 0.05 |
| | 6 | BPADSME | (30) | styrene | (70) | Measurement was impossible due to partial precipitation of crosslinking agent. | | | | |
| | 7 | BPADSME DVB | (15) (15) | styrene | (70) | 15–20 | 120–150 | 90 | 132 | 0.05 |

The abbreviations in Table 3 stand for the following.
DVB: Divinylbenzene
EGDMA: Ethylene glycol dimethacrylate
BPADMA: Bisphenol A dimethacrylate
HDDSME: 1,6-Hexanediol distyrylmethyl ether
BPADSME: Bisphenol A distyrylmethyl ether

EXAMPLES 20–28

The vinylphenyl compound of this invention, a styrene monomer and an ester of a polycyclic hydrocarbon inhibitor. The resultant mixture was charged into a disk on a hot plate adjusted to 100° C. to 130° C. to melt-mix it, and left to stand for 0.5 to 1 hour until it was cured. Then, the disk was placed within an oven at 150° C. for 4 hours to further thermoset the mixture. After it was cured, it was released from the disk to give a transparent plate. Table 5 shows physical properties of the transparent plate obtained in each of the Examples.

For comparison, Table 5 also shows physical properties of polymethyl methacrylate (PMMA), polycarbonate (PC) and diethylene glycol bisallyl carbonate (CR-39).

TABLE 5

| | | Composition (wt. %) | Property | Refractive index | Abbe number | Rockwell hardness (L) | Total light transmissivity (%) | Water absorptivity (%) |
|---|---|---|---|---|---|---|---|---|
| Example | 29 | CS-A*1 100 | colorless transparent solid | 1.648 | 25.4 | 120 | 90 | 0.08 |
| | 30 | CS-A/ethylmethacrylate 100 30 | colorless transparent solid | 1.622 | 28.4 | 104 | 90 | 0.12 |
| | 31 | CS-A/isobornylmethacrylate 70 30 | colorless transparent solid | 1.628 | 27.0 | ~30 | 90 | 0.09 |
| | 32 | CS-A/BP-4EA*2 70 30 | colorless transparent solid | 1.617 | 28.6 | 108 | 90 | 0.11 |
| | 33 | CS-A/DCP-A*3 70 30 | colorless transparent solid | 1.605 | 28.2 | 113 | 90 | 0.10 |
| | 34 | CS-A/maleic anhydride 70 30 | yellow transparent solid | 1.608 | 29.0 | 125 | 85 | 0.14 |
| | 35 | CS-A/diethyl maleate 70 30 | colorless transparent solid | ~1.61 | — | ~40 | 85 | 0.13 |
| | 36 | CS-A/N-phenylmaleimide 70 30 | pale-yellow transparent solid | 1.630 | 27.3 | 123 | 87 | 0.12 |
| Comparative Example | 8 | PMMA | colorless transparent solid | 1.49 | 58 | 100-111 | 91 | 0.30 |
| | 9 | PC | colorless transparent solid | 1.58 | 31 | 95 | 89 | 0.15 |
| | 10 | CR-39*4 | colorless transparent solid | 1.50 | 58 | 99 | 90 | 0.24 |

*1 1,1-bis(4-vinylbenzyloxyphenyl)-1-phenylethane
*2 bisphenol A diethylene glycol diacrylate
*3 bis(oxymethyl)tricyclo[5,2,1,0$^{2,6}$]decane diacrylate
*4 Diethylene glycol bisallyl carbonate

What is claimed is:

1. A polymerizable composition comprising (A) a vinylphenyl compound of the following formula (I)

(I)

wherein $R^1$ is an aryl group having 6 to 12 carbon atoms or an aralkyl group having 7 to 10 carbon atoms, $R^2$, $R^3$, $R^4$, $R^5$ and $R^6$ may be identical to or different from each other and each is a hydrogen atom or an alkyl group having 1 to 4 carbon atoms, and m and n each are independently an integer of not less than 1, and (B) other vinyl compound copolymerizable therewith, the copolymerizable composition containing, based on the total weight of the vinylphenyl compound (A) and the copolymerizable, other vinyl compound (B), 5 to 75% by weight of the vinylphenyl compound (A) and 95 to 25% by weight of the copolymerizable, other vinyl compound (B).

2. A polymerizable composition according to claim 1, wherein the other vinyl compound (B) is at least one compound selected from the group consisting of styrene, acrylate, methacrylate, allyl ether, methallyl ether, maleic acid, maleimide and derivatives of these.

3. A crosslinked polymer comprising polymerized units (A') derived from a vinylphenyl compound of the following formula (I)

wherein $R^1$ is an aryl group having 6 to 12 carbon atoms or an aralkyl group having 7 to 10 carbon atoms, $R^2$, $R^3$, $R^4$, $R^5$ and $R^6$ may be identical to or different from each other and each is a hydrogen atom or an alkyl group having 1 to 4 carbon atoms, and m and n each are independently an integer of not less than 1, and polymerized units (B') derived from other vinyl compound copolymerizable with the above vinylphenyl compound.

4. A thin plate formed of a crosslinked polymer which is a crosslinked polymer recited in claim 3.

5. A thin plate according to claim 4, which is an optical disk substrate.

* * * * *